United States Patent
Beck et al.

(10) Patent No.: US 7,521,926 B2
(45) Date of Patent: Apr. 21, 2009

(54) METHOD FOR TESTING A COMPONENT IN A NON-DESTRUCTIVE MANNER AND FOR PRODUCING A GAS TURBINE BLADE

(75) Inventors: Thomas Beck, Panketal (DE); Ralph Reiche, Berlin (DE); Rolf Wilkenhöner, Kleinmachnow (DE)

(73) Assignee: Siemens Aktiengesellschaft, Munich (DE)

( * ) Notice: Subject to any disclaimer, the term of this patent is extended or adjusted under 35 U.S.C. 154(b) by 423 days.

(21) Appl. No.: 10/525,026

(22) PCT Filed: Aug. 1, 2003

(86) PCT No.: PCT/EP03/08558

§ 371 (c)(1),
(2), (4) Date: Feb. 22, 2005

(87) PCT Pub. No.: WO2004/027217

PCT Pub. Date: Apr. 1, 2004

(65) Prior Publication Data

US 2006/0001420 A1   Jan. 5, 2006

(30) Foreign Application Priority Data

Aug. 23, 2002   (EP) .................................. 02018897

(51) Int. Cl.
G01N 27/72   (2006.01)
(52) U.S. Cl. ....................................... 324/238; 324/228
(58) Field of Classification Search ......... 324/227–241, 324/228–243
See application file for complete search history.

(56) References Cited

U.S. PATENT DOCUMENTS

| | | | |
|---|---|---|---|
| 4,853,634 A | 8/1989 | Tönblom | |
| 5,028,100 A | 7/1991 | Valleau et al. | |
| 5,140,264 A | 8/1992 | Metala et al. | |
| 5,793,206 A * | 8/1998 | Goldfine et al. | 324/242 |

(Continued)

FOREIGN PATENT DOCUMENTS

CH   673 896 A5   4/1990

(Continued)

OTHER PUBLICATIONS

Horst Blumenauer, "Werkstoffprüfung", Deutscher Verlag Für Grundstoffindustrie, 1994, pp. 372-379, Germany.

(Continued)

*Primary Examiner*—Reena Aurora

(57) ABSTRACT

The invention relates to a method for the nondestructive testing of a component, in which corrosion regions close to the surface, composed of oxidized carbides or sulfided base material close to the surface, are determined by means of an eddy current measurement. This allows the blades or vanes to be ground down and/or separated out in particular prior to a complex process of cleaning and coating the gas turbine blade or vane.

15 Claims, 3 Drawing Sheets

U.S. PATENT DOCUMENTS

| | | | |
|---|---|---|---|
| 6,051,972 | A | 4/2000 | Bour et al. |
| 6,534,975 | B2 * | 3/2003 | Beeck et al. ................ 324/230 |
| 6,541,964 | B1 * | 4/2003 | Jourdain et al. ............. 324/232 |
| 2001/0009368 | A1 | 7/2001 | Beeck et al. |

FOREIGN PATENT DOCUMENTS

| | | | |
|---|---|---|---|
| DE | 3517114 | * | 11/1986 |
| DE | 003517114 | A1 * | 11/1986 |
| EP | 1 085 526 | A1 | 3/2001 |
| GB | 227975 | | 1/1925 |
| WO | WO 97/23762 | | 7/1997 |

OTHER PUBLICATIONS

G. Dibelius, H.J. Krichel and U. Reimann, "Non-destructive Testing of Corrosion Effect on High-temperature Protective Coatings", VGB Kraftwerkstechnik 70, 1990, pp. 636-651, No. 9.

Michael J. Woulds, "How to Cast Cobalt-Base Superalloys", Precision Metal, Apr. 1969, pp. 46 and 97.

* cited by examiner

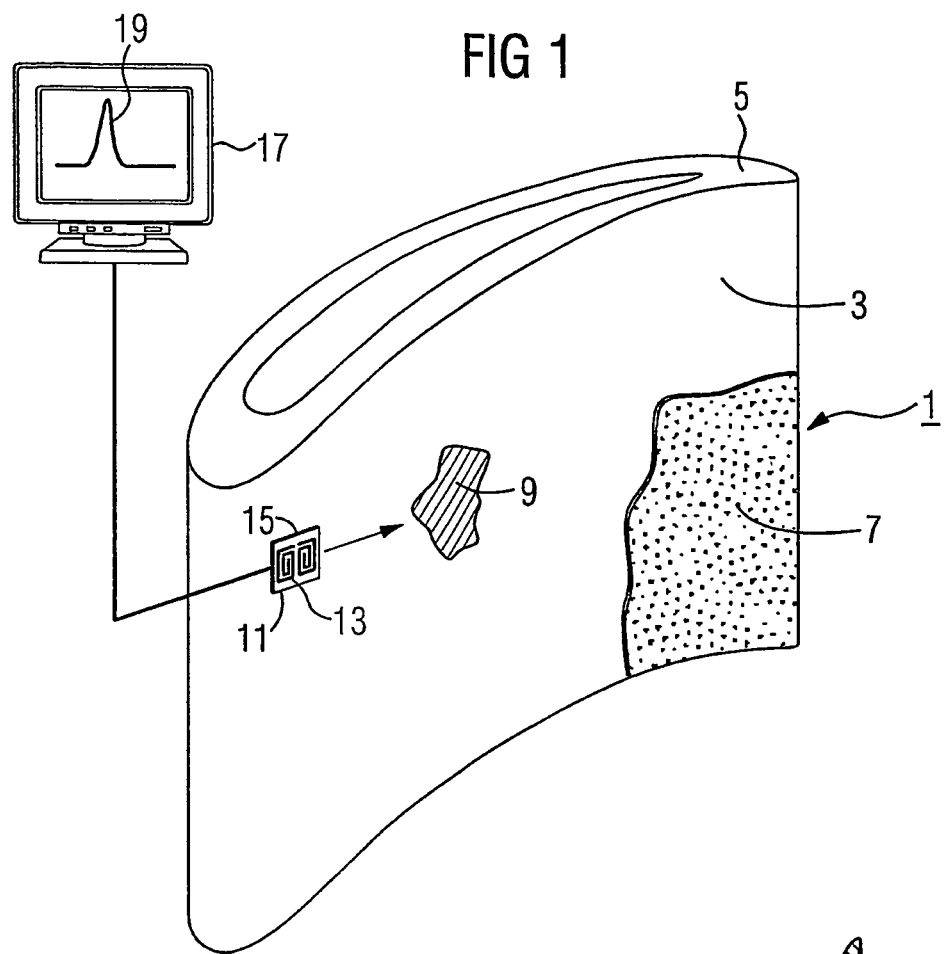
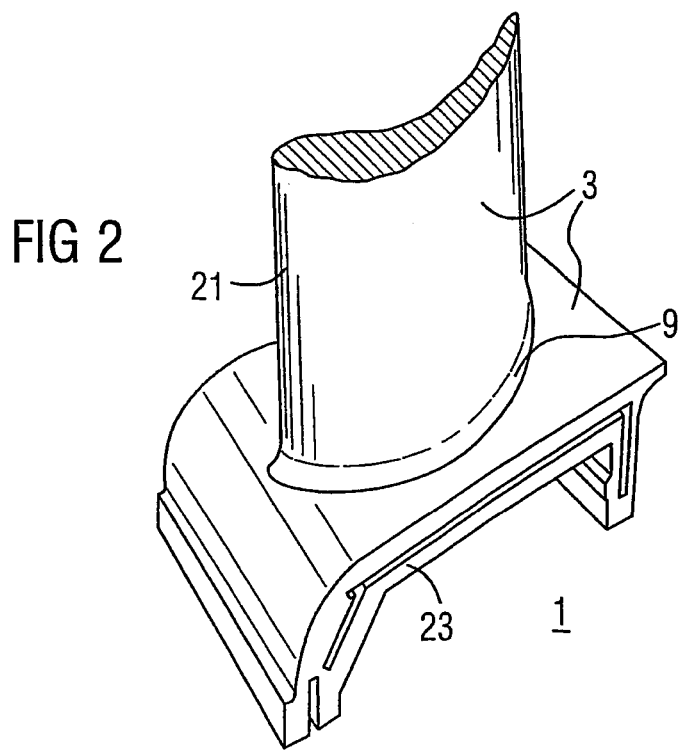

METHOD FOR TESTING A COMPONENT IN A NON-DESTRUCTIVE MANNER AND FOR PRODUCING A GAS TURBINE BLADE

CROSS REFERENCE TO RELATED APPLICATION

This application is the US National Stage of International Application No. PCT/EP2003/008558, filed Aug. 1, 2003 and claims the benefit thereof. The International Application claims the benefits of European application No. 02018897.5 EP filed Aug. 23, 2002, both of the applications are incorporated by reference herein in their entirety.

FIELD OF THE INVENTION

The invention relates to a method for the nondestructive testing of a component. The invention also relates to a method for producing a gas turbine blade or vane.

BACKGROUND OF THE INVENTION

WO 97/23762 discloses a method for layer thickness measurement which is based on an electrically conductive layer being present on a base material; the conductivities of layer and base material must be different. The ratio of the conductivity of layer and base material is limited to a ratio of from 0.7 to 1.5. Moreover, in particular eddy currents in a range from 1.5 to 3.5 MHz are used.

GB 22 79 75 A1 describes conductivity measurements in the region close to the surface for materials with a high magnetic permeability, which can only be tested in magnetic saturation.

U.S. Pat. No. 5,793,206 describes a measurement probe for layer thickness measurement.

These methods and/or the probes have the drawback of only being able to determine layer thicknesses.

The book "Werkstoffprüfung" [materials testing], 5th Edition, VEB Deutscher Verlag für Grundstoffindustrie, Leipzig 1989, by H. Blumenauer, describes the nondestructive testing of materials using the eddy current method. It is based on the electromagnetic alternating field of a coil through which alternating current is flowing changing when a metallic specimen is brought into its region of action. The primary field of the coil induces an AC voltage in the specimen that is to be tested, and this voltage in turn generates an alternating current, which for its part then generates a magnetic alternating field. This secondary alternating field counteracts the primary field in a characteristic way and thereby changes its parameters. The change can be recorded by measurement means. For this purpose, for example in the case of coils with a primary and secondary winding, the secondary voltage is measured (transformer principle). Alternatively, for example in the case of coils with only one winding, the impedance thereof is determined (parametric principle). According to the laws which apply in an alternating current circuit, the induction in the coil and in the specimen, in the case of the parametric arrangement, in addition to the ohmic resistance, also generates an inductive resistance and, in the case of the transformer arrangement, generates an imaginary measurement voltage as well as the real measurement voltage. Both components are presented in complex form in the impedance plane or the complex voltage plane. In both these examples, the nondestructive testing of materials makes use of the effect whereby the changes in the primary field are dependent on the physical and geometric specimen properties and also on the apparatus properties. Apparatus properties include the frequency, the current intensity, the voltage and the number of windings of the coil. Specimen properties include electrical conductivity, permeability, specimen shape and material inhomogeneities in the region of the eddy currents. More recent appliances for inductive testing allow measurements at a plurality of excitation frequencies. For this purpose, by way of example, the frequency during a measurement can be altered automatically, or the frequency is adjusted manually by the user during two measurements. The frequency has a considerable influence on the penetration depth of the eddy currents. Approximately the following relationship applies:

$$\delta = \frac{503}{\sqrt{f \cdot \sigma \cdot \mu_r}}$$

[mm] penetration depth,
f[Hz] frequency,
[MS/m=m/($\Omega$mm$^2$)] specific conductivity,
$\mu_r$ relative permeability.

The standard penetration depth decreases as the frequency rises.

The article "Non-Destructive Testing of Corrosion Effect on High Temperature Protective Coatings" by G. Dibelius, H. J. Krischel and U. Reimann, VGB Kraftwerkstechnik 70 (1990), No. 9, describes the nondestructive testing of corrosion processes in protective layers on gas turbine blades and vanes. A measurement method used for nickel-based protective layers is measurement of the magnetic permeability, on account of the ferromagnetism changing during the corrosion process, i.e. the material has a very high relative magnetic permeability (>100-1000), in the protective layer. The possibility of eddy current measurement is discussed for the case of a platinum-aluminum protective layer system. The layer thickness of the protective layer can be worked out on the basis of the measured signal levels.

The article "How to cast Cobalt-Based Superalloys" by M. J. Woulds in: Precision Metal, April 1969, p. 46, and the article by M. J. Woulds and T. R, Cass, "Recent Developments in MAR-M Alloy 509", Cobalt, No. 42, pages 3 to 13, describe how the solidifying or solidified component surface can react with the material of the cast shell during the casting of components and also gas turbine blades and vanes. This can, for example, lead to the oxidation of carbides in the cast component. A phenomenon of this type is also referred to here as "Inner Carbide Oxidation", ICO. The formation of ICO leads to carbides which reinforce the grain boundaries of an alloy breaking down.

In particular in the region of a gas turbine blade or vane which is close to the surface, this can lead to considerable weakening of the material. The alloys are usually cast using vacuum casting. The oxygen which is required for oxidation is derived from the material of the casting shell, e.g. silicon dioxide, zirconium dioxide or aluminum oxide. As a result, oxide phases are formed on the grain boundaries. The original carbides are transformed, for example, into zirconium-rich, titanium-rich or tantalum-rich oxides. The depth of the region which contains oxidized carbides is dependent on parameters such as the carbon content in the alloy, the composition of casting shell material and casting alloy, and also the cooling rate. An oxide-containing layer of this type may typically be approximately 100 to 300 µm thick. For quality control, it is desirable for it to be possible to detect the oxide regions of oxidized carbides which have an adverse effect on the mechanical properties. This has not hitherto been possible by nondestructive testing.

Under certain environmental conditions, nickel- and cobalt-base alloys tend to form a form of corrosion known as high-temperature corrosion (HTC). From a materials science perspective, HTC is a complex form of sulfiding of the base material which takes place at the grain boundaries. As HTC progresses, supporting cross sections of components are weakened. It is important to know the depth of the HTC attack in order to allow the operating safety and remaining service life of a component to be estimated and in order to decide whether rework (e.g. refurbishment of gas turbine blades or vanes) is possible.

SUMMARY OF THE INVENTION

Therefore, it is an object of the invention to provide a measurement method which can also be used to determine high-temperature corrosion (degraded regions) of a component, which forms in particular along grain boundaries. Furthermore, it is an object of the invention to provide a method for producing a gas turbine blade or vane, in which a corrosion-resistant layer is applied to a base body of the gas turbine blade or vane, in which case the quality and service life of the corrosion-resistant layer are particularly high.

According to the invention, these objects are achieved by the methods as described in the patent claims. Advantageous refinements of the invention will emerge from the subclaims.

According to the invention, the object directed at a method for the nondestructive testing of a component is achieved by a method for nondestructive testing in which two different measurement frequencies are used.

According to the invention, the object directed at a production method is achieved by a method for producing a gas turbine blade or vane, in which a base body of the gas turbine blade or vane is cast, the surface of the base body is cleaned and activated for the application of a corrosion-resistant layer, and then the corrosion-resistant layer is applied, with the surface being tested for the presence of oxide regions of oxidized carbides by means of an eddy current measurement after the casting operation and prior to cleaning and activation.

Particularly in the case of a gas turbine blade or vane, the high thermal an d mechanical loads mean that a defect-free microstructure of the base material is particularly important. In this region, therefore, quality testing for ICO-containing and/or corroded regions is of considerable value.

The alloy is preferably a nickel-base or cobalt-base superalloy. Superalloys of this type are best known in gas turbine construction and are distinguished in particular by a particular ability to withstand high temperatures. However, these superalloys especially have a tendency to react with the oxygen of the casting molds during casting and thereby to form the abovementioned ICO regions.

Corrosion-resistant layers which are applied to a base body are often used for gas turbine blades or vanes. The base body is preferably formed from a nickel- or cobalt-base superalloy. Furthermore, it is preferable for the corrosion-resistant layer to be selected from an alloy of the MCrAlY type, where M is selected from the group consisting of iron, cobalt and nickel, Cr is chromium, Al is aluminum and Y is yttrium selected from the group consisting of yttrium, lanthanum, rare earths. A protective layer of this type requires a preliminary treatment of the surface of the base body in order to ensure permanent bonding between the base body and the protective layer. A suitable cleaning process which simultaneously activates the surface for good bonding to the protective layer is a sputtering process, in which ions are accelerated onto the base body surface and thereby clean and activate the surface by means of their kinetic energy. Tests have shown that ICO regions in the surface layer prevent suitable cleaning and activation of the base body surface. The ICO regions cannot be removed by the sputtering process. They are uncovered correctly, since metal or impurities which have partially covered them are preferentially removed, but the oxides themselves are not. This has a significant adverse effect on the bonding of the corrosion-resistant layer to the blade or vane base body.

Eddy current measurement is used to make it possible to ascertain whether ICO-containing regions are present at the surface of the base body of a gas turbine blade or vane even before the complex cleaning and coating process. This for the first time makes it possible to effect advance cleaning of the blades or vanes with ICO-containing regions by means of a grinding process at low cost or even to separate out such blades or vanes in advance. Blades or vanes which have been successfully cleaned or blades or vanes which do not include any ICO regions from the outset are then provided with the corrosion-resistant layer, preferably by plasma spraying.

The composition of the base body superalloy is preferably as follows (details in percent by weight):

24% of chromium, 10% of nickel, 7% of tungsten, 3.5% of tantalum, 0.2% of titanium, 0.5% of zirconium, 0.6% of carbon, remainder cobalt. This alloy is also known under the tradename MAR-M 509.

BRIEF DESCRIPTION OF THE DRAWINGS

The invention is explained in more detail, by way of example, with reference to the drawing, in which, in some cases diagrammatically and not to scale:

FIG. 1 shows a method for testing a gas turbine blade or vane for ICO regions,

FIG. 2 shows a gas turbine blade or vane with visible ICO regions,

DETAILED DESCRIPTION OF THE INVENTION

Figure 3:
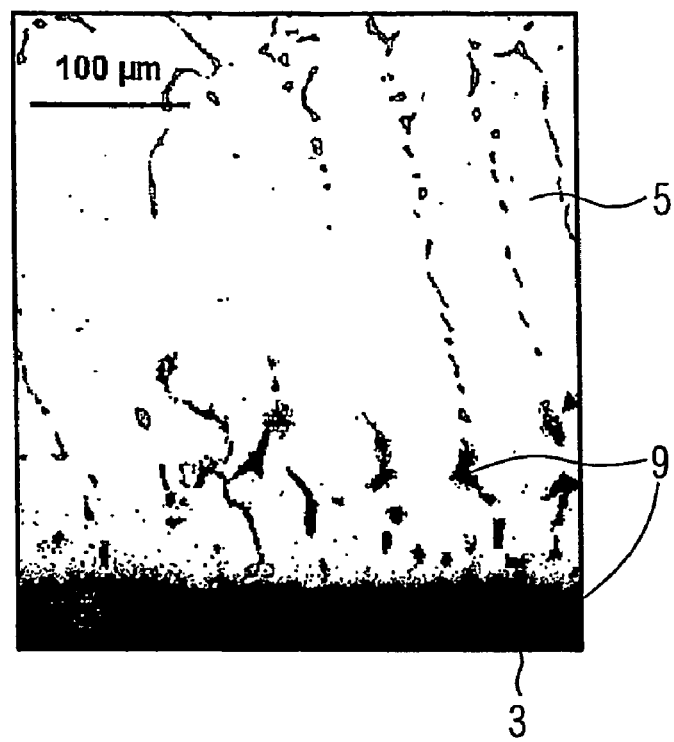
FIG. 3 shows part of a longitudinal section through the base body of a gas turbine blade or vane having an ICO layer.

Identical reference symbols have the same meaning throughout the various figures.

Surprisingly, it has emerged that the degraded regions, in particular the oxide regions of oxidized carbides (ICO, cf. above) or the corrosion regions of sulfided base material, can be detected with sufficient accuracy by means of an eddy current measurement. An eddy current measurement of this type is based, as stated above, in particular on the electrical conductivity within the degraded or ICO regions being different than that of the base material. Furthermore, tests have been able to demonstrate that the sensitivity of the method is even sufficient to allow determination of the depth of the ICO-containing regions which are present (for example whether they are arranged in layer form or are present to a certain layer thickness). As stated above, this requires eddy current measurements at different excitation frequencies (measurement frequencies). At suitably low frequencies, the eddy current propagation in the ICO-containing region is negligible, and consequently the measurement is determined only by the properties of the base material. In a transition range, the change in the primary field is caused by the eddy currents both in the unaffected base material and in the ICO-containing region. Beyond a certain frequency level, the eddy current field propagates only within the ICO-containing region. Accordingly, there is a defined transition in the measurement variable (e.g. conductivity or permeability) as a function of the excitation frequency. The depth of the ICO-containing region can be determined by correlating the frequency at which the influence of the ICO-containing layer is dominant with the depth of penetration of the eddy current field.

FIG. 1 diagrammatically depicts a method for the nondestructive testing of a component 5, in particular a gas turbine blade or vane 1, by means of an eddy current testing method. The gas turbine blade or vane 1 has a surface 3. A protective layer 7 is applied to the surface 3 in a subregion; this protective layer 7 is included in FIG. 1 for the sake of completeness, even though this protective layer 7 is actually only applied after the eddy current testing has been carried out. A degraded region, for example a corrosion region 9 or an oxide region 9 of oxidized carbides, has formed in the surface 3 as a result of a reaction with a mold shell (not shown) in the casting process used to cast the gas turbine blade or vane 1. Reaction with oxygen from this mold shell has caused carbides to be converted into oxides in this corrosion region 9 or oxide region 9. A corrosion region 9 may also have been formed from sulfided base material in the surface 3 as a result of high-temperature corrosion, for example in use.

This on the one hand leads to a reduction in the strength of the base body in this region, since the action of the carbides of strengthening the grain boundaries is eliminated. A further result of this is that a cleaning and activation process by means of sputtering, which takes place prior to the application of the protective layer 7, has no effect in the corrosion region 9. This has a considerable detrimental effect on the bonding of the protective layer 7 to the base body 5.

An eddy current measurement method is used to determine disruptive corrosion regions 9 even prior to the complex cleaning and coating process. For this purpose, an eddy current probe 11 is guided over the surface 3, bearing directly on the surface 3. Electrical coils 13 are arranged on a flexible plastic carrier 15 and a magnetic field is generated through the coils 13 by means of an alternating current. This induces electric currents in the surface 3 and these electric currents are in turn fed back into the coils 13 via their magnetic field. This is made visible as a signal 19 in an evaluation unit 17 which is connected to the eddy current probe 11. A signal 19 of different intensity results depending in particular on the electrical conductivity but also on the magnetic permeability of the material in the region of the eddy current probe 11. The corrosion region 9 can be detected by means of the eddy current probe 11 on account of having a different electrical conductivity and magnetic permeability.

Furthermore, the depth of the corrosion region 9 can be determined by changing the frequency in the alternating field of the eddy current probe 11. It is therefore possible for the first time to detect corrosion regions (ICO) 9 by nondestructive testing. This in particular has considerable cost benefits, since the blades or vanes can be ground clean or separated out before a complex cleaning and coating process.

FIG. 2 shows ICO regions 9 which have become visible in a gas turbine blade or vane 1 following a cleaning and activation process by means of sputtering. The ICO regions 9 are in this case concentrated in particular in a transition region between the main blade or vane part 21 and the securing region 23.

FIG. 3 illustrates a longitudinal section showing the form of an ICO region 9 at the surface 3 of the component 5. The component 5 consists of the abovementioned MAR-M 509 cobalt-base superalloy. The thickness of the ICO layer is approx. 100 μm.

Figure 4:
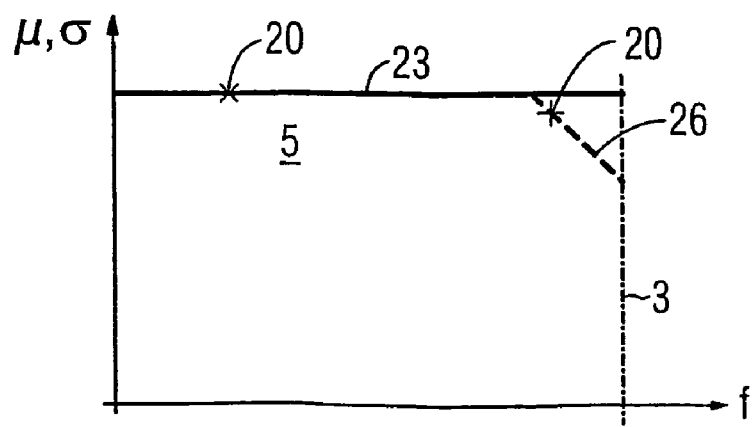
FIG. 4 shows measurement curves which are determined using the method according to the invention, FIG. 5 diagrammatically depicts a region close to the surface of a component which is degraded.

FIG. 4 shows the measurement curves which are determined using the method according to the invention. The magnetic permeability $\mu$ (and from this the relative magnetic permeability $\mu_r$) or the electrical conductivity ($\sigma$) is determined as a function of the frequency f. The materials used have a very low magnetic permeability $\mu_r$, approximately equal to 1 (1.001) or at most 1.2.

A measurement probe (FIG. 6) is placed onto the base material or the substrate, with the frequency f then being changed in a range from 500 kHz to 35 MHz.

The higher the frequency, the smaller the volume of interaction produced by the eddy currents becomes.

Therefore, at least two measurement points 20 are measured. At low frequencies f, the interaction volume is very large, so that it is almost exclusively only the properties of the base material that are measured and changes in these variables in the region close to the surface are negligible. This type of measurement is comparable to that achieved with an uncorroded base material.

The measurement curve 23 of the base material is therefore determined even by a single measurement point, since this results in a parallel to the frequency axis. However, it is also possible to incorporate even more measurement points 20 to determine the parallels.

Having started with low frequencies f, i.e. large interaction volumes (penetration depths), which show only the properties of the substrate, the frequency f is increased further (second measurement point), with the result that the interaction volume (penetration depth) becomes smaller. The interaction volume becomes so small that it is virtually exclusively in the region of the surface 3 of the component 5. By way of example, degraded, i.e. corroded, oxidized or sulfided regions are present exclusively or very often in this very region. The magnetic permeability or electrical conductivity of these degraded regions has changed and results in a deviation in the measurement curve 26 of the component 5.

Therefore, the properties of the base material and the position and size of the corroded regions can be determined in a frequency scan. The region to be tested does not have to be in magnetic saturation.

Figure 5:
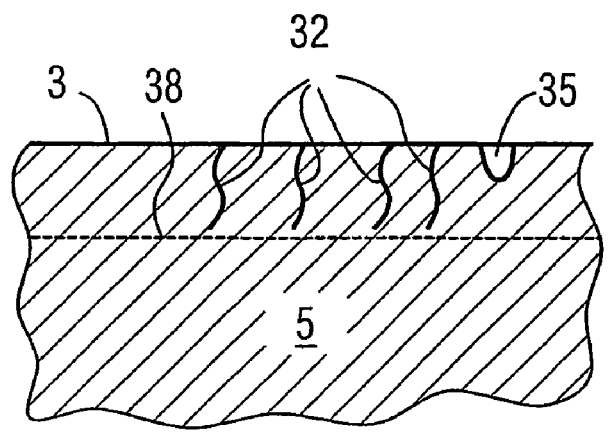

FIG. 5 shows a region close to the surface of a component which is corroded. Starting from the surface 3, there are grain boundaries 32 which are oxidized, corroded or degraded in some other way. These may also represent oxidized precipitations. Holes 35, at which material has already broken out of the surface 3, may also be present in the region of the surface 3. If the frequency f is selected to be sufficiently high, the interaction volume 38 is formed such that it adjoins the corroded regions 9. The measurement signal is then influenced to a greater extent by the corroded grain boundaries 32 and the holes 35. This change is recorded by the measurement signal and demonstrates that there is a defect in the component or substrate.

Figure 6:
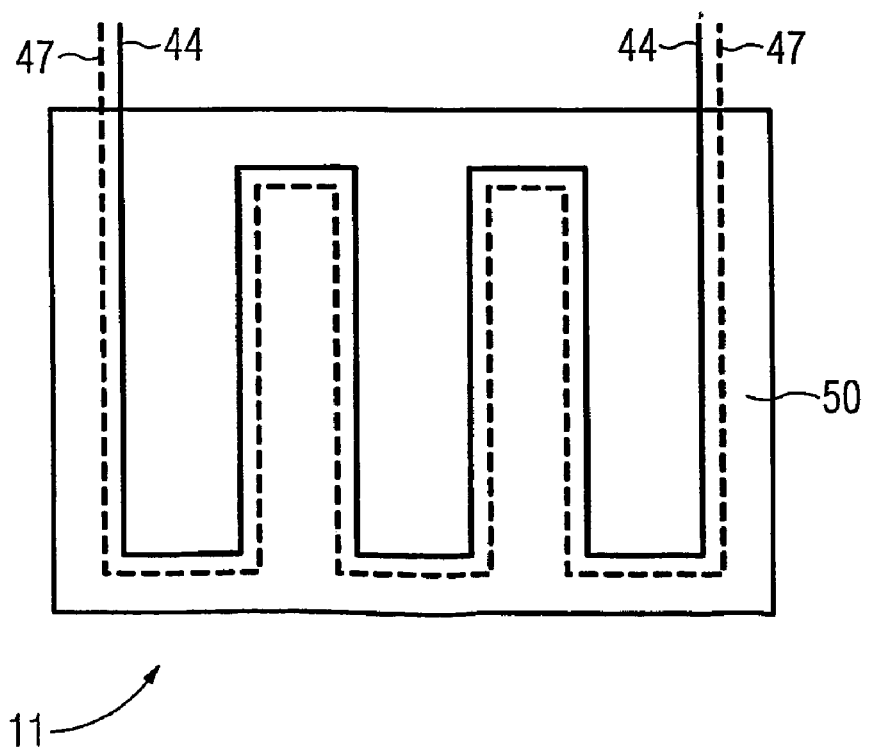
FIG. 6 shows an example of a probe used for the method according to the invention.

FIG. 6 shows an example of a probe 1 which is suitable for this measurement method. An exciter coil 44 and a signal coil 47 are arranged in meandering form on a substrate or sheet 50. For more details on the arrangement and functioning of the coils, reference is made to U.S. Pat. No. 5,793,206. This patent is hereby expressly incorporated by reference in the disclosure of the present application. Contrary to the previous use of this probe (layer thickness measurement), different frequencies f are applied to this coil 11, as has already been described in FIG. 4.

The invention claimed is:

1. A method for the nondestructive testing of a component comprising a base body further comprising a base material, the method to determine a degraded region of the base material, comprising:

subjecting the component to a first eddy-current producing signal of a first frequency;

determining a property of the base material responsive to the first signal having a depth of penetration including the base material;

subjecting the component to a second eddy-current producing signal of a second frequency, the first frequency lower than the second frequency;

subjecting the component to additional frequency signals continuously from the first frequency to the second frequency, wherein the subjecting of the component to said additional frequency signals comprises performing a frequency scan from the first frequency to the second frequency; and determining a property of the degraded region responsive to the second signal having a depth of penetration including the degraded region, wherein the property of the degraded region comprises conductivity or permeability, wherein the base body and the degraded region do not contain ferromagnetic material.

2. The method as claimed in claim 1, wherein the first signal comprises a low frequency signal and the second signal comprises a high frequency, and wherein the component is initially subjected to the first signal followed by the second signal.

3. The method as claimed in claim 1, wherein oxide regions composed of oxidized carbides that are near a surface of the base body represent the degraded regions.

4. The method as claimed in claim 1, wherein the base body comprises a carbide-containing alloy.

5. The method as claimed in claim 1, wherein sulfided regions of the base body located close to a surface of the base material represent the degraded regions.

6. The method as claimed in claim 1, wherein a measurement probe with coils in meandering form is used to generate the first and the second signals.

7. The method as claimed in claim 1, wherein a relative magnetic permeability of the base body is less than or equal to 1.2.

8. The method as claimed in claim 1, characterized in that the frequency of each of the first and the second signals is in the range from 500 kHz to 35 MHz.

9. The method as claimed in claim 1, wherein the measurement probe for the eddy current measurement is located on a surface of the base body.

10. The method as claimed in claim 1, wherein the base material is made from a nickel- or cobalt-base superalloy.

11. The method as claimed in claim 1, wherein the degraded regions have a low electrical conductivity.

12. The method as claimed in claim 1, wherein a measurement variable of the base material is measured responsive to the first signal and a measurement variable of the degraded region is measured responsive to the second signal.

13. The method as claimed in claim 12, wherein the measurement variable changes during the eddy current measurement as a function of the frequency.

14. The method as claimed in claim 1, wherein the component is a blade or vane.

15. The method of claim 1 further comprising determining a depth of the degraded region according to a difference between the property of the base material and the property of the degraded region.

* * * * *